(12) United States Patent
Spahn

(10) Patent No.: US 7,747,058 B2
(45) Date of Patent: Jun. 29, 2010

(54) IMAGE PROCESSING METHOD FOR WINDOWING AND/OR DOSE CONTROL FOR MEDICAL DIAGNOSTIC DEVICES

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 944 days.

(21) Appl. No.: 11/529,640

(22) Filed: Sep. 28, 2006

(65) Prior Publication Data

US 2007/0076937 A1   Apr. 5, 2007

(30) Foreign Application Priority Data

Sep. 30, 2005   (DE) .................. 10 2005 047 539

(51) Int. Cl.
*G06K 9/00* (2006.01)
(52) U.S. Cl. ....................... 382/132; 382/168
(58) Field of Classification Search ................ None
See application file for complete search history.

(56) References Cited

U.S. PATENT DOCUMENTS

| | | | |
|---|---|---|---|
| 4,827,492 A | 5/1989 | Klauzs | |
| 5,150,421 A | 9/1992 | Morishita et al. | |
| 5,351,306 A | 9/1994 | Finkler et al. | |
| 5,867,593 A | 2/1999 | Fukuda et al. | |
| 2003/0165216 A1* | 9/2003 | Walker et al. | 378/108 |
| 2005/0010106 A1* | 1/2005 | Lang et al. | 600/425 |
| 2005/0063579 A1* | 3/2005 | Lee et al. | 382/131 |

FOREIGN PATENT DOCUMENTS

| | | |
|---|---|---|
| DE | 197 42 152 A1 | 3/1999 |
| EP | 0 811 289 B1 | 10/2001 |
| EP | 1 040 649 B1 | 2/2002 |

OTHER PUBLICATIONS

Rafael C. Gonzalez and Richard E. Woods, "Digital Image Processing", 1992, pp. 31-39, Addison-Wesley.
"Flachbilddetektoren in the Röntgendiagnostik", Flat Panel Detectors in x-ray diagnostics, Radiologe, 2003, pp. 340-350, vol. 43.

* cited by examiner

*Primary Examiner*—Charles Kim

(57) ABSTRACT

Image processing method for determining and setting an optimized windowing and/or dose control of a medical diagnostic device based on x-ray radiation. The digitized image consisting of a number of picture elements of an picture data matrix B originally created by an x-ray detector is processed. The object area is determined by forming an input picture data matrix B1, by forming an ROI picture data matrix B2, by analysis of the ROI picture data elements and by selection of the ROI picture data elements belonging to the object area, and in that the signals of the ROI picture data elements of the object area are evaluated.

18 Claims, 5 Drawing Sheets

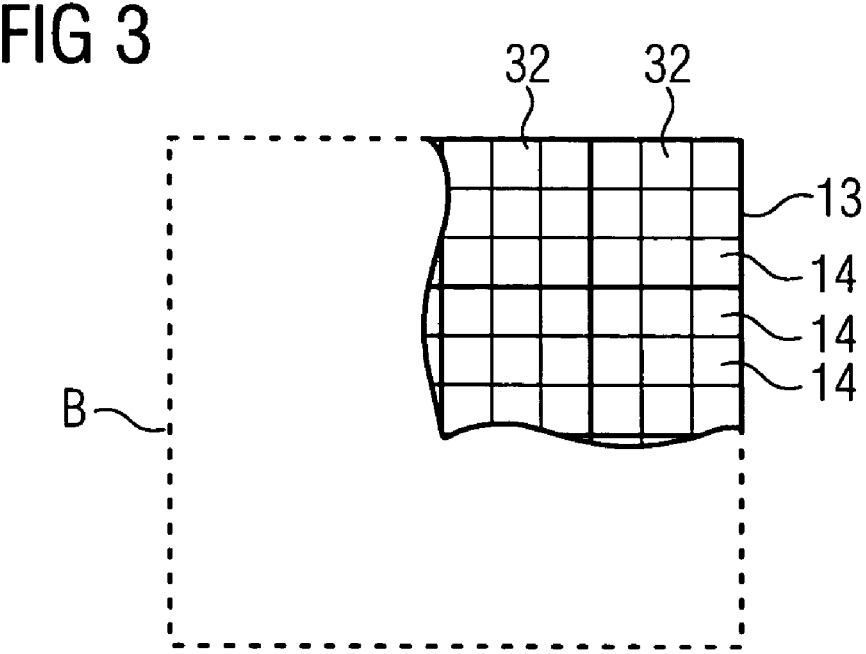
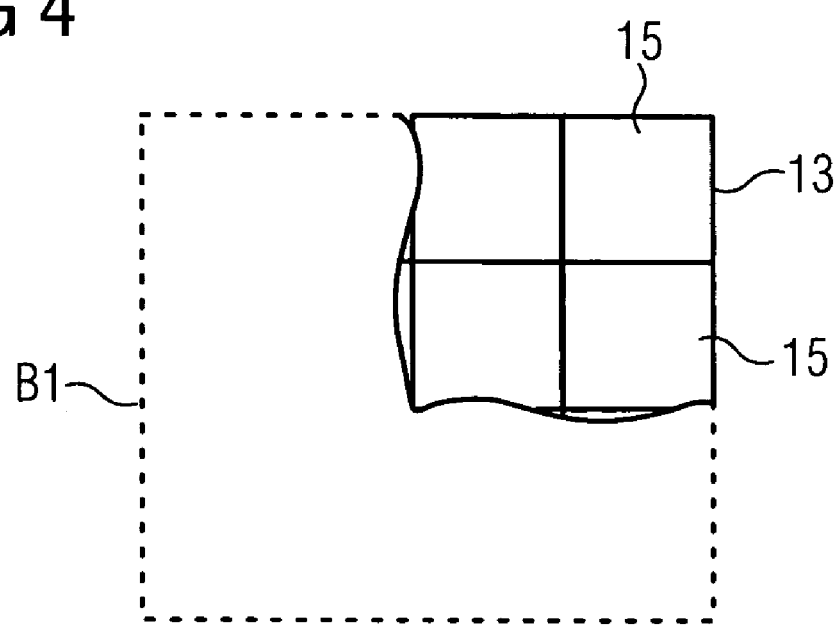

IMAGE PROCESSING METHOD FOR WINDOWING AND/OR DOSE CONTROL FOR MEDICAL DIAGNOSTIC DEVICES

CROSS REFERENCE TO RELATED APPLICATIONS

This application claims priority of German application No. 10 2005 047 539.6 filed Sep. 30, 2005, which is incorporated by reference herein in its entirety.

FIELD OF THE INVENTION

The invention relates to an image processing method for determining and setting optimized windowing and/or dose control for medical diagnostic devices, especially digital flat-panel detectors based on x-ray radiation.

BACKGROUND OF THE INVENTION

Digital imaging methods have now come to play a decisive role in medical diagnostics and intervention. Whereas digital techniques have been used from the start in diagnostic methods such as in computer tomography, magnetic resonance, ultrasound and in nuclear medicine, the transition to digital imaging is now taking place to a large extent in "conventional" x-ray methods, such as mammography, angiography or cardiology. Digital x-ray detectors have thus been changing classical radiography for many years. A very wide variety of technologies have already been in use for a long time or are due on the market very soon. These digital technologies include systems such as image intensifier camera systems, based on television or CCD (Charged Coupled Devices) cameras, memory foil systems with integrated or external read-out unit, systems with optical coupling of the converter foil to CCDs or CMOS chips, selenium-based detectors with electrostatic readout or solid-state detectors with active readout matrices and direct or indirect conversion of the x-ray radiation. The last-mentioned solid-state detectors (FD) in particular have undergone extensive development in recent years for use in digital x-ray imaging. A detailed overview of different systems or the general operation of direct or indirect-operation solid-state detectors is given in "Flachbilddetektoren in the Röntgendiagnostik" (Flat Panel Detectors in x-ray diagnostics), Radiologe 43 (2003) P. 340-350).

The permanent request from practical user experience is for better editing of the digital image in order to present the diagnostic content to its optimum effect and thereby to simplify and to accelerate diagnosis. Furthermore a significant objective of digital image processing is the editing of the x-ray image to reduce the radiation burden on the patient and on the examiner. In this case image processing functions as an intermediary in cases in which image information is present in a form which is inaccessible to the eye as a result of physiological characteristics of human vision. In addition to resolution, two significant parameters for an optimum image adjustment are the signal level and the contrast. In this case what is known as windowing provides assistance in compensating for the contrast capability of the eye which is restricted to appr. $2^7$-$2^8$ gray levels, in that a spreading of the subareas of the image over the entire light density area of the illumination medium is undertaken and thereby its full dynamics exploited. With the current high digital resolution which is already the norm of up to 14 bits and thereby 16384 gray levels, the parameters for windowing are becoming even more important. If the windowing is too narrow or if the optimum level is not selected, image content disappears, if windowing is too wide the image contrast is too low and details are more difficult to distinguish. As already mentioned at the start, with x-ray devices on the other hand with almost delay-free digitization, such as for example with x-ray devices with flat-panel detectors, image processing is used to make dose control (e.g. for fluoroscopic examinations at high image rates of approximately 30 images/s) possible. In this case the image content is analyzed automatically and the generator settings (e.g. high voltage, tube current, filter) are obtained for the subsequent series of images. At this point this control task must even be performed by a digital image processing, since unlike with older technologies of image amplifiers, no separate optical signal can be derived here which would be able to be used for control tasks.

Various options are known from the prior art for setting the correct window values. Thus U.S. Pat. No. 4,827,492 describes a device for manual gray value windowing in which the window width is set with one operating element and the center of the window, the upper or the lower window border are set with another operating element. However processes which execute automatically are desirable which save time and money in clinical operation.

Another widespread option for automatic windowing in x-ray systems is the exclusive use of so-called organ buttons which use a preset, empirically-determined set of parameters for the relevant recording area. The disadvantage of this process is the high operator effort caused by the organ buttons. Furthermore the imaging conditions which differ individually because of the previously defined parameters are not taken into account, the parameters set can thus only represent a compromise.

A method is described in U.S. Pat. No. 5,351,306 in which, by determining statistical parameters in evaluation fields extending lengthwise in parallel to the border of the image, the position of insertions can be found. This fact that overradiation remains unconsidered and rotated insertions cannot be detected means that the optimum results are not always obtained with this type of windowing.

A method is known from U.S. Pat. No. 5,150,421 in which the histogram compensation described in literature and generally known (even distribution of the grey values) is performed in a slightly modified form. With this non-linear gray value transformation a restriction to the relevant image area is however also necessary. This is resolved by weighting the individual pixels differently. A requirement is that insertions and overradiation are extremely bright or dark and are also mainly to be found at the edges of the image. Pixels close to the edge of the image as well as those with extreme grey values are also weighted less for histogram compensation than those which lie closer to the center of the image or which have less extreme grey values. Furthermore an object contours detection is proposed which is based on the detection of large changes to gray values in the image. The disadvantages of such a method are that this non-linear gray value transformation changes the character of the image. Furthermore it is not always true to assume that relevant areas of the image always lie close to the center of the image or do not have any extreme gray values. In addition insertions cannot be reliably detected by an object contour detection simply by detecting large gray value changes in the image without further measures.

A method is known from DE-A1-197 42 152 for windowed presentation of medical images in which insertions and/or overradiations can be recognized and extracted and only for the relevant parts of the image recorded in this way can their window sizes be determined by determining their minimum and maximum values. In these cases overradiation and/or insertions are completely extracted by recognizing geometrical structures, which also causes the removal of pixels in the edge area of the relevant parts of the image. Furthermore a method is described through which, starting from the edge areas, insertions, caused by a diaphragm can be extracted. In this case pixels are investigated step-by-step to the center of the image to see if they exceed a threshold as regards their gray value. The approaches described here refer back to the recognition of geometrical structures, edges, contours.

SUMMARY OF THE INVENTION

The object of the invention is to specify a further-developed method which in a simple and robust manner separates diagnostic content of x-ray images from non-diagnostic content in order to achieve an optimum image reproduction and windowing. In this case especially direct irradiation areas or areas which are covered by tube-side diaphragms as well as transitional or edge areas of the relevant areas for imaging with diagnostic content are to be separated from the object area. Furthermore the object of the invention is to define the remaining diagnostic image areas so that they can be used for controlling the radiation dose.

The object is achieved by an image processing method for determining and setting an optimum windowing and/or dose control, especially of images of a medical diagnostic device based on x-ray radiation, whereby the digitized image consisting of a number of pixels of an original picture data matrix B created by an x-ray detector, especially a flat panel detector, is processed by the following steps:

1. Determining the object area by:
   1a) Forming an input picture data matrix B1 starting from the original detector picture data matrix B;
   1b) Combining a number of pixels of the input picture data matrix B1 into areas of interest and creating an ROI picture data matrix B2 consisting of these ROI picture data elements, in which case each pixel of the input picture data matrix is only involved once in forming an ROI picture data element;
   1c) analysis of the individual ROI picture data elements of the ROI picture data matrix B2;
   1d) Selection of the ROI picture data elements of the object area; and
2. Signal evaluation of the ROI picture data elements of the object area In this case the original detector picture data matrix B is the picture data matrix essentially directly recorded via the x-ray detector, which is subsequently reduced and simplified and investigated with regard to its object area of interest. Depending on detector size, resolution and intelligence a compressed input picture data matrix B1 is produced after a first possible iteration step and after a second iteration step an ROI picture data matrix B2 which contains as its elements what are referred to as Region Of Interest (ROI) image elements. This advantageously both minimizes the amount of data which enters further analysis and also achieves a certain smoothing of the output data. With the analysis of the ROI picture data elements these can now be clustered and divided into different areas. By division into the areas a decision is made as to whether the ROI picture data elements belong to an object area which is of further interest and is to be included in further observation or whether it should be discarded. The extraction of ROI picture data elements of interest is followed by settings for determining the object area. In further evaluations the data from the object area can also be used for controlling the radiation dose, especially for sequential multiple recordings. The method is essentially based on the fact that clinical objects generally exhibit structures i.e. edges or gray value changes (bones, vessels etc.). Direct radiation areas or inserted regions are by contrast very homogeneous, do not have any such structures and in addition have either very high signals (direct radiation area) or very low signals (diaphragm area).

It has proved advantageous for the input picture data matrix B1 to be formed by reducing the number of pixels. In current flat panel detectors measuring 40×40 cm, over 7 million pixels are produced in the first detector picture data matrix B for a pixel size of approximately 150 µm. A first reduction of this volume of data appears sensible, especially to guarantee examinations with high image rates (e.g. 30 images) because of the restrictions in performance arising.

In an advantageous embodiment of the invention, the reduction of the number of pixels for forming the input picture data matrix B1 is undertaken by what is referred to as undersampling of the original detector picture data matrix B. In this case the original detector picture data matrix B is rastered into subareas, in which case these previously defined and as a rule static, equal-size and non-overlapping subareas are assembled from a specific number of pixels of the original detector picture data matrix B. From these subareas any given pixel or a pixel which is always located at the same position in the subarea is used representatively for generating the input picture data matrix B1. The total of the individual pixels taken from the subareas forms the input picture data matrix B1. This embodiment variant represents a very simple and high-performance but at the same time often sufficient method for first reduction of the original volume of image data.

In a further advantageous embodiment, a reduction of the number of pixels for forming the input picture data matrix B1 is generated by what is referred to as binning. In this process a pixel is again obtained for forming an input picture data matrix B1 from the previously-described subareas. This time however the pixel of the input picture data matrix B1 is calculated from the signal levels (gray values) of all pixels of the relevant subarea. The sum of the pixels calculated for the relevant subarea forms the input picture data matrix B1 for the further algorithm. Different options are conceivable for the calculation of the relevant pixels representing the subarea, which enables the pixels belonging to the subarea to be weighted differently. The advantage of this embodiment is an improvement of the database for the further algorithm since no pixels are discarded but all pixels are included in the formation of the input picture data matrix.

In a further advantageous embodiment of the invention, it is proposed that the pixel of this subarea which is used to create the input picture data matrix B1 is calculated by forming the average of the signal levels of all pixels of the relevant subarea. Such averaging can be performed very quickly and forms the subarea for the further algorithm with sufficient quality.

In an advantageous embodiment of the invention it has proved sufficient and advantageous for the subarea to have a size of 3×3 pixels up to 15×15 pixels. This means that on the one hand the number of pixels can be a significantly reduced by a factor 9-225 without on the other hand important information being lost. Furthermore, this allows the algorithm to be well matched to the available computing power.

In another embodiment of the inventory a first compression of the original detector picture data matrix B can already be undertaken by algorithms in the detector and thereby by the detector itself. In the case in which the detector only provides a compressed detector picture data matrix this becomes the input picture data matrix B1 directly for subsequent method steps. In such a case the method step for forming the input data matrix B1 in the downstream digital image processing system can be almost switched to inactive because of the 1:1 relationship between subarea and pixels of the compressed data image matrix, and nothing changes in the algorithm itself. A control and adaptation to the pre-compression by the detector is then undertaken in these cases exclusively via the parameters supplied.

In a further advantageous variant an ROI picture data element is formed from the combination of 5×5 to 50×50, preferably 10×10 to 30×30 pixels of the input picture data matrix B1. This produces for example with the previously-mentioned detector data and subareas of 3×3 pixels a spectrum of appr. 300 to 30,000 ROI picture data elements. The precise number of the ROI picture data elements is governed by parameters such as complexity, resolution or contrast of the image.

In an advantageous variant of the invention the analysis of the individual ROI picture data matrix is undertaken by evaluating its frequency spectrum. To do this the ROI picture data elements which are presented in the time or space area as a series of gray values are transferred into what is referred to as the frequency area in which not only the gray values themselves but the frequency and phase components of the underlying sequences of gray values are mapped. A frequency image is thus produced for each ROI, as is generally known from the prior art. In this case large jumps in the grey value sequences are mapped via high frequencies, soft gray value transitions are equal to low frequencies. Furthermore diffraction effects, as inevitably occur in the diaphragm area, can be interpreted directly for example as intensity distribution of the Fourier transforms. Thus the evaluation of the frequency spectrum enables deductions to be made about edge areas caused by diaphragms. FFT (Fast Fourier Transformation) is to be specified as representing a possible algorithm for performing Fourier transformation. Other algorithms known to the person skilled in the art would be conceivable.

A further embodiment is produced if the evaluation of the frequency spectrum is related to the undershooting or exceeding of the threshold values. The frequency analysis can additionally be optimized by the knowledge of the organ to be examined. For example bone structures (e.g. knee, foot, hand etc.) will contain many more high frequency components than a soft tissue (abdomen). The typical detector mentioned above can resolve with a pixel size of 150 µm ideally and without aliasing effects local frequencies of up to 3.3 lp/mm (line pairs per millimeter). An observed organ with bone structures, such as a knee for example, will typically feature local frequencies of up to 3 lp/mm or more. These local frequencies then correspond to the object area, whereas direct irradiation or diaphragm areas will only have very small local frequencies (approaching 0 lp/mm). Further-developed, high-resolution detectors with a pixel size of for example up to 50 µm, as are preferably used in mammography, naturally need other threshold value parameters. In this way the assignment of the individual analyzed ROI picture data elements to pre-defined areas is easily possible.

In a further advantageous embodiment the analysis of the individual ROI picture data elements of the ROI picture data matrix is undertaken by evaluating their signal level compared to the histogram distribution of the input picture data matrix B1. The histogram forms all grey values from black to white in its range of values depending on the digital gray value resolution of the detector (analog-digital converter). Each ROI picture data element is now analyzed in respect of the range of values into which it falls. A relatively narrow lower range of values will correspond to the diaphragm area, a relatively narrow upper range of values to the direct irradiation area. The transitional areas directly adjoin diaphragm and direct irradiation area. The object region of interest thus lies between the transitional areas.

In an especially preferred embodiment the signal level is evaluated by comparison with the histogram distribution such that the signal levels of the ROI picture data elements, which are formed from the arithmetic mean of the individual pixels involved in the formation of the ROI image elements, the input picture data matrix B1, and which lies in the range of values from 10-70% of the histogram will be assigned to the object area. In a further subdivision a lower area of the histogram from 0-5% is assigned to the diaphragm area, an upper area of the histogram from 95-100% to the direct irradiation area. The areas from 5-10% as well as from 70-95% belong to the transitional areas. In this way ROI picture data elements can be assigned very easily and rapidly in a simple and high-performance manner to an object area. In further embodiments these area boundaries are also able to be variably adjusted.

In a further advantageous embodiment the analysis of the individual ROI picture data elements by ROI picture data matrix B2 is undertaken by the evaluation of the signal width function. In this case the signal of an ROI picture data element, i.e. its average grey value in the exemplary embodiment, is logically combined with the width of the ROI picture data element which is defined by the difference between the maximum and the minimum signal within this ROI picture data element. ROI picture data elements in diaphragm areas will have both small widths and also small signal values, ROI picture data elements in direct irradiation areas can likewise be expected to have small widths but high signal values. ROI picture data elements in transition areas, especially between diaphragm and direct irradiation area, will again feature large widths with average signals. Assignments to typed areas can thus be made from the position of the individual ROI picture data elements in the signal width diagram. Other calculation options are however also possible for determining the signal value and/or the width of the ROI picture data elements. Thus, for example, a signal value formed from the median can be calculated or the width is produced by the standard deviation ó, of the square root of the variance, that is of the second central moment. The values for signal level and width determined in this way can likewise be the basis for the evaluation of the signal width function. All the above-mentioned analysis methods have in common that they can be used in a simple manner for clustering of ROI picture data elements and thereby for extracting the image content relevant for further consideration.

In a further very advantageous embodiment of the invention, the above-mentioned analysis methods can be combined in any way with each other according to the frequency spectrum, according to the signal level compared to the histogram distribution and according to the signal width function. In this case two of the above-mentioned analysis methods or even all three analysis methods can be combined with each other. The accuracy of the statements made is further improved by a combination of the analysis methods, since disadvantages of the individual methods can be compensated for in this way.

In another preferred embodiment, the evaluation results for the individual ROI picture data elements from the frequency analysis and/or histogram distribution and/or signal width analysis form a number of input nodes of a neuronal network. The output node of this neuronal network then supplies information about which area (direct irradiation, diaphragm area, transitional or object area) the ROI picture data elements can be most probably assigned to. Input variables for the input nodes of the neuronal network represent for example the peak frequency of Fast Fourier Transformation or the relative signal level in relation to the histogram or the signal width function. If the knowledge of the organ to the examined by means of the organ programs is additionally to be provided as input value, the known organ represents a further option for supply to an input node.

In a further embodiment of the invention, the ROI picture data elements of the object area recognized are included for determining and setting an optimum dose performance of the x-ray radiation. In a first step, the arithmetic means of the individual ROI signal level of the object area are formed, the relevant mean represents the ROI picture data element with a value. According to a few embodiments of the invention (e.g. histogram distribution analysis), these values are already available and can be referred back to. In a further step a specific q-quantile of the series of ROI image data elements arranged in order of their signal level is determined so that the relative frequency of the underlying values is at least q. The value of the quantile is reconciled with the sensitivity of the detector for the x-ray spectrum used. It has for example proved advantageous to set the q-quantile to the 25 percent quantile. The reconciliation produces a value for the system dose arriving at the detector and in downstream processes lying outside the scope of the invention and therefore not explained in further detail here, generator settings such as high-voltage tube current, filter are obtained for example.

In a further embodiment of the invention, the ROI picture data elements of the detected object area are included for determining and setting an optimum windowing. Accordingly, as previously described the arithmetic means of the individual signal levels of the ROI picture data elements of the object are formed in a first step. The lower window value is now produced from a value lying in the range of values from 0-10% of the histogram, the upper window area from a value lying in a range of values from 90-100% of the histogram of all ROIs of the object area. In this case the above-mentioned percentage figures of 0 and 100% do not relate to the full dynamics of the detector but, as upper and lower limits, represent the actual grey range of the object area. Thus the grey range of the identified object area is spread once again which results in a further improved image presentation in the object area. It has proved advantageous to set the lower window area to the value of 5%, the upper window area to the value of 95%.

The invention is to be explained in greater detail below with reference to exemplary embodiments. The Figures show:

DETAILED DESCRIPTION OF THE DRAWINGS

Figure 1:
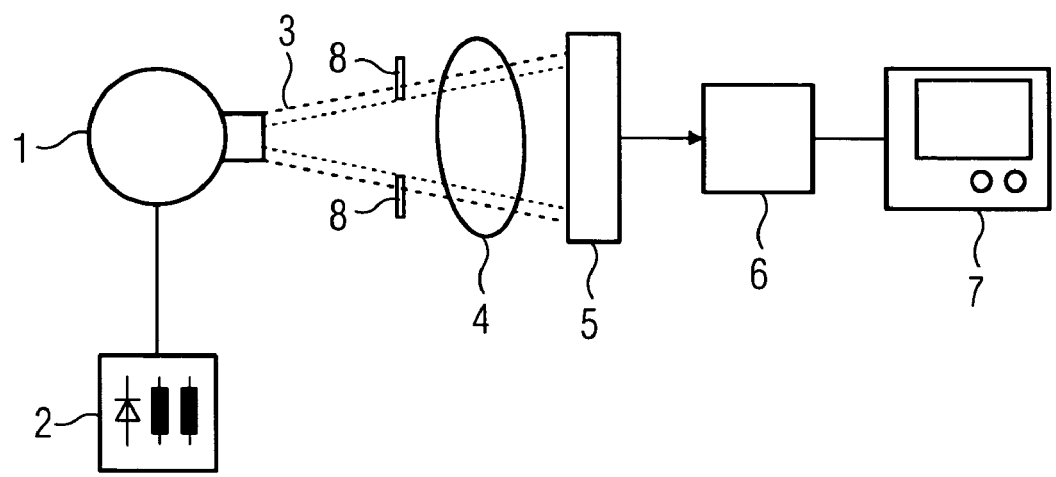
FIG. 1 an x-ray diagnostic device in accordance with the prior art,
FIG. 2 x-rays of a knee to identify areas
FIG. 3 an original detector picture data matrix B
FIG. 4 a pixel-reduced input picture data matrix B1
FIG. 5 an ROI picture data matrix B2 and its formation
FIG. 6 an image in accordance with FIG. 2 with ROI picture data matrix B2
FIG. 7 analysis method for ROI picture data elements
FIG. 8 a schematic diagram of the neuronal network

FIG. 1 shows the electrical layout of an x-ray diagnostic device. An x-ray tube 1 is operated by a high-voltage generator 2. The x-ray tube 1 emits a bundle of x-rays 3 which penetrate a patient 4 and falls on an x-ray detector 5 weakened in accordance with the transparency of the patient 5 and forms an x-ray image. The absorption of the x-ray radiation 3 by the patient 4 follows an exponential function. The x-ray detector 5 converts the x-ray image into electrical signals which are processed in a connected digital image processing system 6 and are fed to a monitor 7 for reproduction of the x-ray image. By insertion of diaphragms 8 the x-ray bundle can be influenced so that it penetrates the patient 5 to a restricted extent and the load does not fall onto the fully active surface of the x-ray detector 5. The x-ray detector 5 can, as described above, either consist of a flat panel detector of the type described at the start or of a unit comprising x-ray image amplifier, optics and downstream camera (television or CCD camera). In both cases a digital image signal of the entire active surface of the detector is made available to the image processing system 6. The number of pixels (picture elements) of the digitized image is governed by the size of the active detector surface and resolution of the detector, the number of gray levels is governed by the quality of the upstream analog-digital converter used to form the digitized image. In a known way, the digital image system 6 can feature processing circuits, converters, differential stages or image storage.

Figure 2:
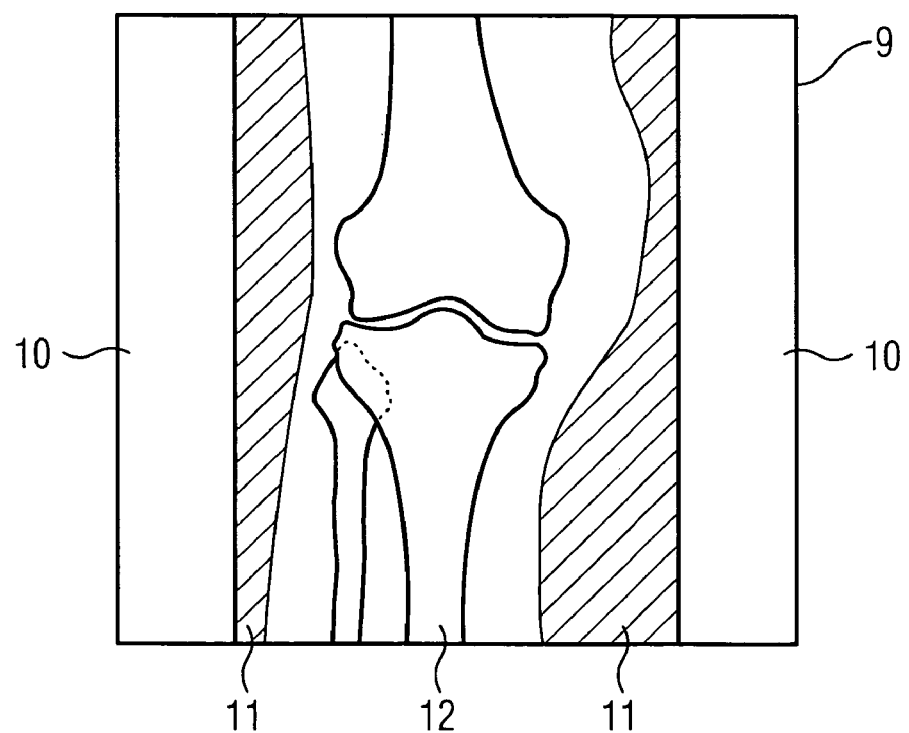

FIG. 2 shows a typical image of a knee. In this case the surface 9 represents the entire active detector surface of the x-ray detector 5. The area 10 is the diaphragm area collimated by the diaphragms 8 which will be shown white in the image. The area 11, as the direct irradiation area, represents the area of the image in which the x-ray bundle 3 falls directly, i.e. without being attenuated by the patient 4 on the surface 9 of the x-ray detector 5. The object area 12 is the remaining area which falls more or less attenuated by the patient 4 onto the detector surface 9. The digitized image of this common detector surface 9 is referred to below as the original detector picture data matrix B.

FIG. 3 shows an original detector picture data matrix B. This is made up of a series of picture elements 14. For a flat-panel detector with an active detector surface of 40×40 $cm^2$, for a size of the photodiodes of appr. 150 µm, which each represent a picture element, a pixel quantity of appr. 7 million picture elements is produced. FIG. 3 shows a small section 13 of the original detector picture data matrix B consisting of picture elements 14. A number of picture data elements 14 are combined into subareas 32.

FIG. 4 shows the input picture data matrix B1 with the identical section 13. The input picture data matrix B1 is now represent by a smaller number of picture elements 15 compared with the picture data matrix B, with a picture element 15 being representative of a subarea 32. In the example shown in FIG. 4 a picture element 15 is formed by 3×3 picture elements 14 (FIG. 3). This reduction of the number of pixels can be produced by undersampling or binning, in which case different binning algorithms are conceivable. A few x-ray detectors already able to reduce the number of pixels by themselves. In such an example a reduction of the number of pixels does not then have to be undertaken in the image processing system 6.

Figure 5:
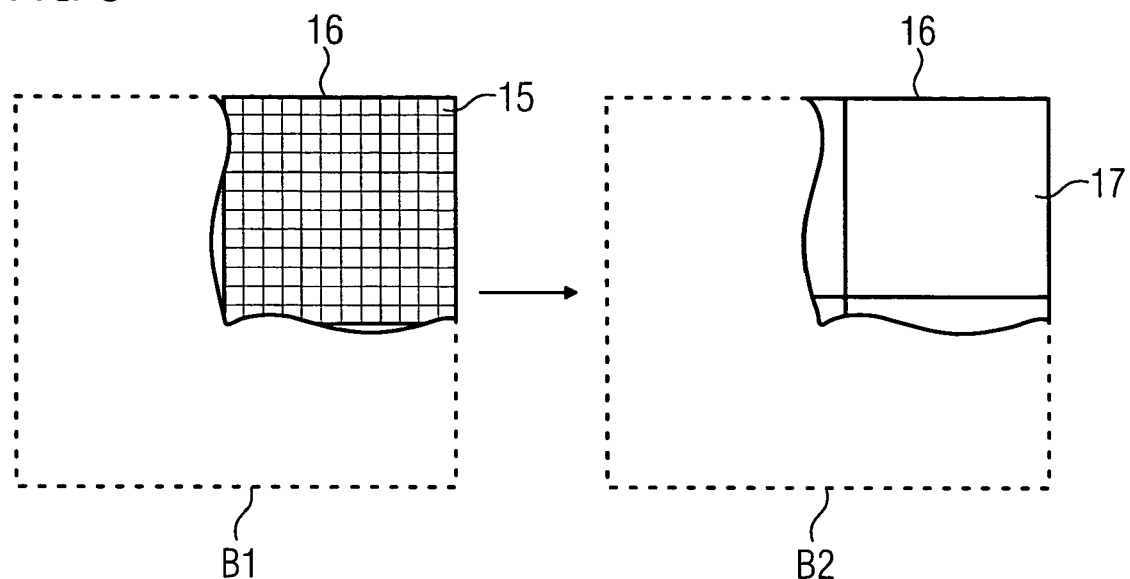

FIG. 5 shows the formation of an ROI picture data matrix B2 which has been produced from the input picture data matrix B1. The enlarged section of the input picture data matrix B2, by contrast with the enlarged section 16 shown in FIGS. 3 and 4, shows a number of picture elements 15. Several picture elements 15 are combined to form regions of interest 17 (ROI, Region Of Interest). In accordance with FIG. 5 10×10 picture elements 15 are typically combined to form an ROI picture data element 17. These ROI picture data elements 17 are subsequently subjected to analyses in order to assign ROI picture data elements 17 to one of the above-mentioned areas and to filter out the ROI picture data elements 17 which definitively represent the object area.

Figure 6:
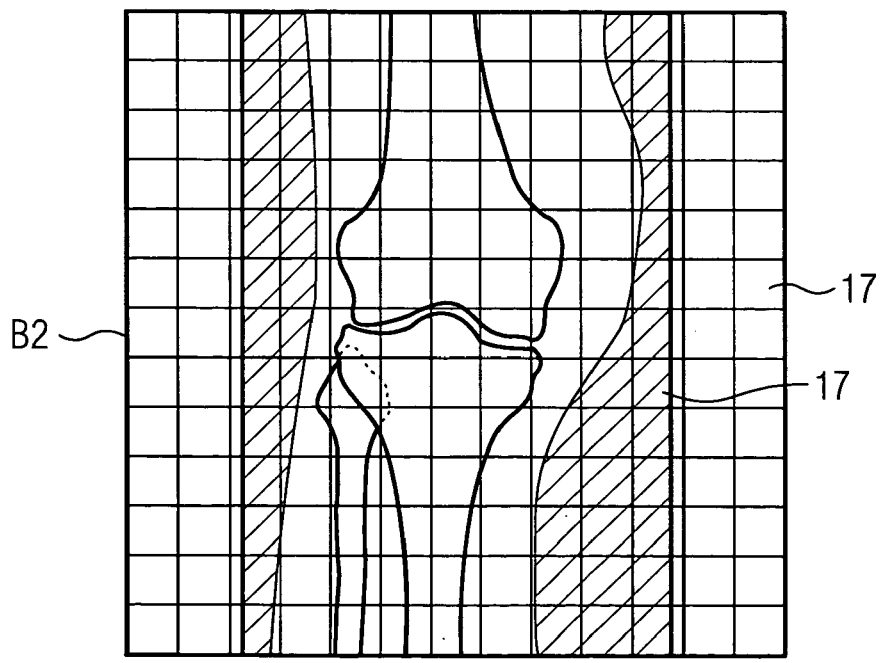

FIG. 6 shows the image of the knee shown in FIG. 2 as ROI picture data matrix B2 with its ROI picture data elements 17.

Figure 7:
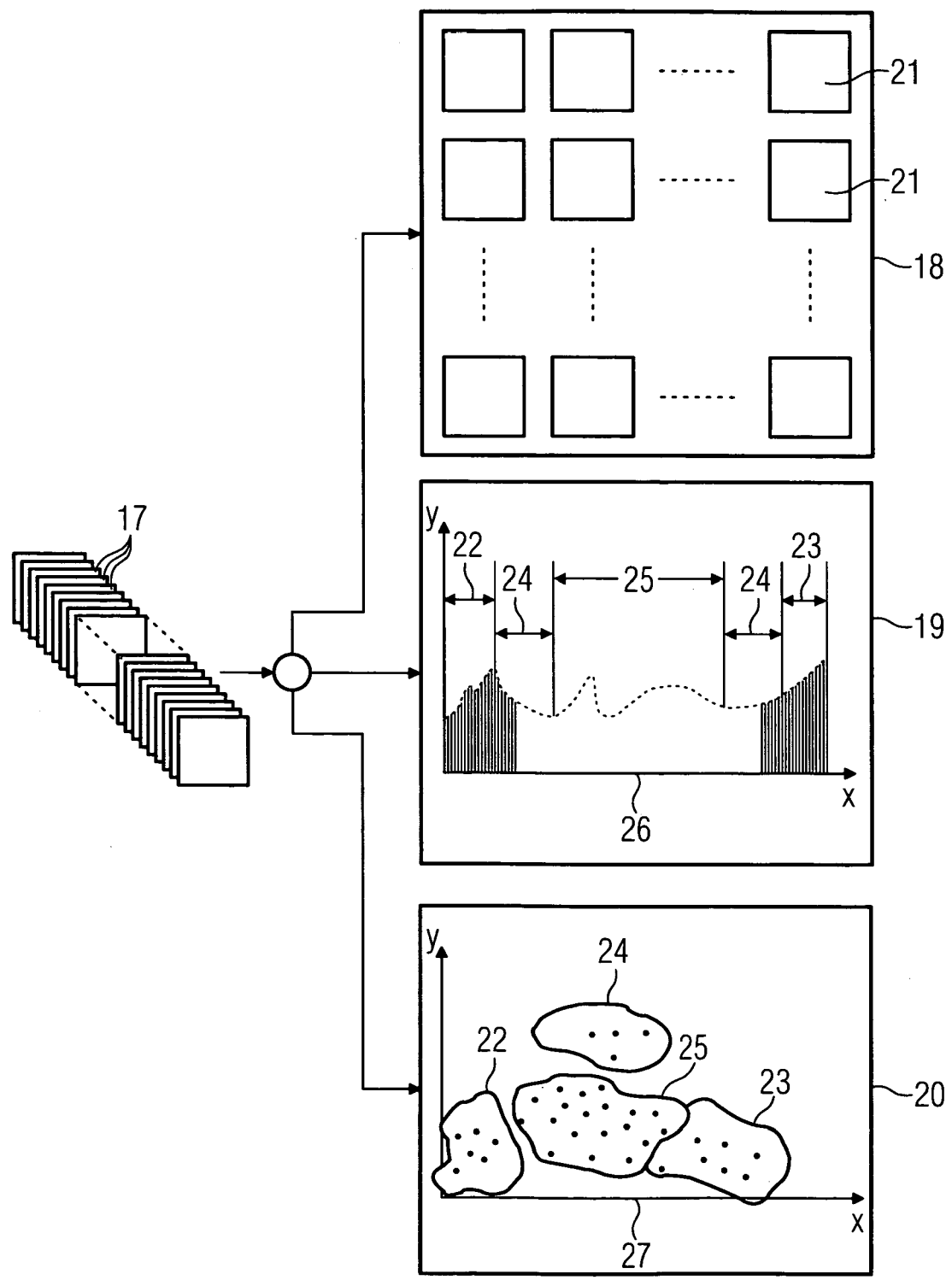

In the analysis method which is shown schematically in FIG. 7, each of the ROI picture data elements 17 is subjected to a frequency spectrum analysis 18, a histogram distribution analysis 19 and/or a signal width analysis 20. Each of the frequency images 21 has originated from an ROI picture data element 17, for which an assignment to the relevant areas (diaphragm, direct radiation, transition or object area) can now be made. In another analysis method, the histogram distribution analysis 19 the signal levels of the ROI picture data elements 17 are considered by comparison with the histogram distribution of the overall pixel matrix of the input picture data matrix B1. In this case the signal value is plotted on one axis and the frequency on the other axis. To do this the signal level (e.g. arithmetic mean of the signal levels of the picture elements 15) of each ROI picture data element 17 is formed and compared, in which range of values of the histogram 26 the input picture data matrix B1 of these signal levels falls. In this case the histogram 26 in the range of values from 0 and 100% does not map the full dynamics of the detector, but represents as lower and upper limits the actual gray range of the input picture data matrix B1 and thereby only a reduced dynamic range of the detector. The range of values between 0 to 5% is assigned to the diaphragm area 22, the range of values 95 to 100% to the direct irradiation area 23, the range of values from 10-30% and 70-95% to the transition areas 24 and the range of values from 30-70% to the object area 25. Since the absorption of the x-ray radiation in the body of a patient follows an exponential function the typical percentage values mentioned above relate to a logarithmically-divided scale for the range of values. In another variant the range is divided up on the basis of calculations of the quantiles, with below the 5% quantile being assigned to the diaphragm area 22 and above the 95% quantile to the direct irradiation area 23. In a third analysis method, the signal width analysis 20, the ROI picture data elements 17 are analyzed in respect of their signal width values. In this case the signal value is plotted on the x axis and the width on the y axis. The signal value of the ROI picture data elements 17 (see e.g. arithmetic mean) so and the width value of the ROI image data element 17 (gap between minimum and maximum signal level of the picture element 15 within an ROI picture data element 17) are computed and can be presented graphically as shown for example in the signal width diagram 27. This enables the ROI picture data elements to be assigned to the various areas. Such limits are depicted schematically in diagram 27 as the areas 22 (diaphragm area), 23 (direct radiation area), 24 (transition area) or 25 (object area).

Figure 8:
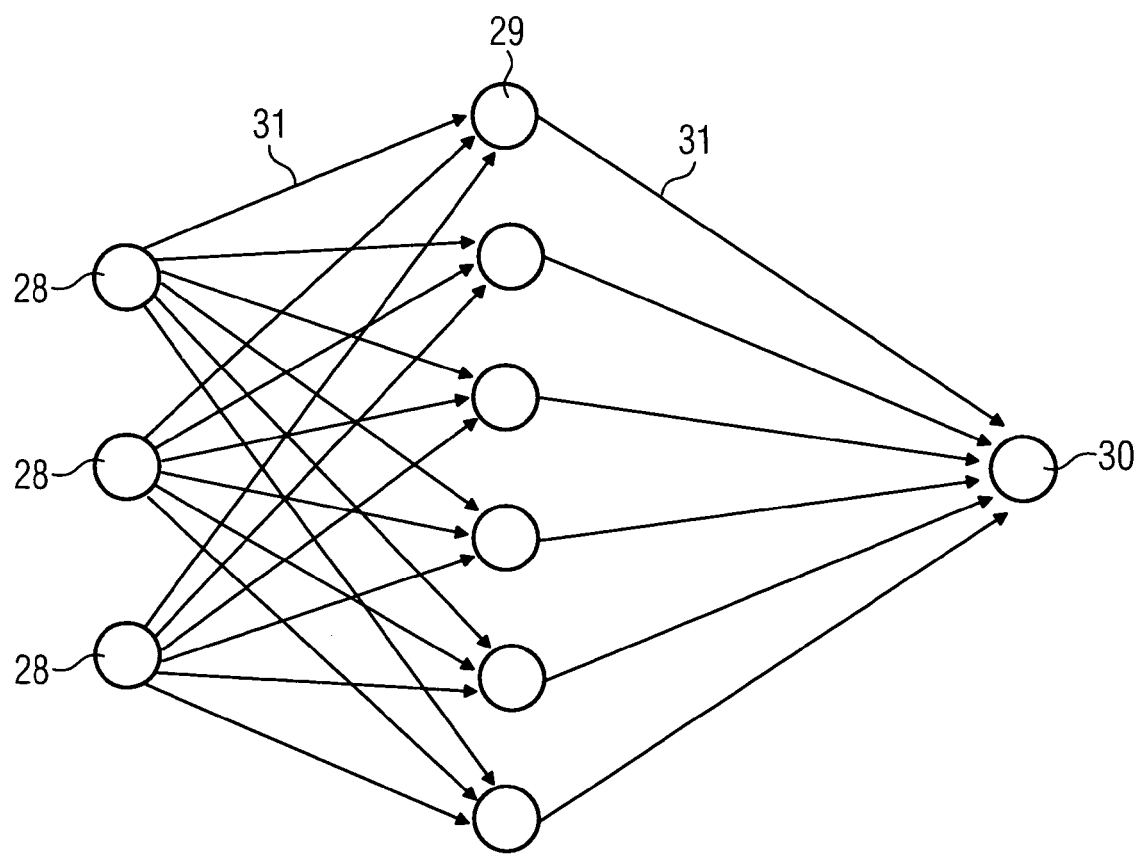

FIG. 8 shows schematically the structure of a neuronal network, consisting of a number of neurons, as is known from the prior art. The neurons of the input nodes (input units) 28, are fed with signals or patterns of the outside world, the intermediate nodes (hidden units) 29 contain an internal representation of the outside world, the output node (output units) 30 returns signals to the outside world. The information flow and connecting arrows 31 between the neurons represent the connections between the neurons, known as the connectors. The strength of the connection is expressed using a weight. The input units are supplied with results of frequency analysis, histogram analysis and/or signal width analysis. If the different areas (diaphragm area, direct irradiation area, transition area, object area) are assigned class or area numbers from 1-4, the output units deliver a probability distribution of the classes/area numbers 1-4. ROI picture data elements which in this way are assigned non-Integer area values by the neuronal network can thus be assigned to the most probable area by rounding up or rounding down of these non-Integer area values.

The invention claimed is:

1. An image processing method for determination and setting of an optimized windowing of images of a medical diagnostic device based on x-ray radiation, wherein a digitized image comprises a number of picture elements of a picture data matrix B originally created by an x-ray detector, the method comprising:

composing the picture data matrix B to include at least an object area, at least a diaphragm area, and at least a direct irradiation area, wherein each of said respective areas has a different response to x-ray radiation passing through the respective areas, wherein respective picture data elements corresponding to said at least object area, said at least diaphragm area, and said at least direct irradiation area generate respective signals having different characteristics based on the different responses of the respective areas to the passing x-ray radiation, wherein the picture data matrix B is processed to identify among the respective areas said at least object area using the following steps:

forming an input picture data matrix B1 starting from the original picture data matrix B;

combining a number of pixels of the input picture data matrix B1 into Regions Of Interest (ROI);

creating an ROI picture data matrix B2 comprising ROI picture data elements, wherein each pixel of the input picture data matrix B1 is only involved once in the formation of an ROI picture data element;

analyzing the individual ROI picture data elements of the ROI picture data matrix B2 to assign ROI picture data elements likely to correspond to one of said at least object area, said at least diaphragm area, and said at least direct irradiation area, wherein the analyzing of the individual ROI picture data elements of the ROI picture data matrix B2 comprises evaluating respective signals generated by the ROI picture data elements of the ROI picture data matrix B2, the evaluating based on the different responses of the respective areas to the passing x-ray radiation; and based on results from the evaluating of the respective signals generated by the ROI picture data elements of the ROI picture data matrix B2, selecting the ROI picture data elements of said at least object area, and discarding ROI picture data elements of said at least diaphragm area and said at least direct irradiation area wherein analyzing the individual ROI picture data elements further comprises:

a frequency spectrum analysis that compares the frequency components of said individual ROI picture data elements to predefined threshold values;

a histogram distribution analysis that determines a histogram range for each of said respective areas; and a signal width analysis that analyzes the signal widths of said individual ROI picture data elements.

2. The image processing method according to claim 1, wherein the input picture data matrix B1 forming step comprises, forming the input picture data matrix B1 by reducing the number of pixels of the original picture data matrix B.

3. The image processing method according to claim 2, wherein the reducing step comprises, reducing the number of pixels for forming the input picture data matrix B1 with a given pixel of each subarea by undersampling the original picture data matrix B, wherein the undersampling comprises, dividing the original picture data matrix B into a number of non-overlapping subareas, wherein case each subarea consists of a number of pixels of the picture data matrix B.

4. The image processing method as claimed in claim 3, wherein the subarea has a size of 3×3 to 15×15 pixels.

5. The image processing method according to claim 2, wherein the reducing step comprises, reducing the number of pixels for forming the input picture data matrix B1 with one pixel in each subarea by combining a number of pixels (Binning) of the original picture data matrix B, wherein the combining comprises dividing the picture data matrix B into a number of non-overlapping subareas, wherein each subarea comprises a number of pixels of the picture data matrix B and wherein the pixel is computed from the signal level of all pixels of the relevant subarea.

6. The image processing method according to claim 5, wherein calculating the pixel of the subarea used in creating the input picture data matrix B1 is by forming the arithmetic mean of all pixels of the relevant subarea.

7. The image processing method according to claim 5, wherein the forming the input picture data matrix B1 step, comprises forming the input picture data matrix B1 by the x-ray detector itself.

8. The image processing method according to claim 1, wherein the ROI creating step comprises, forming an ROI picture data element of the ROI picture data matrix B2 from the combination of 5×5 to 50×50 adjacent pixels of the input picture data matrix B1.

9. The image processing method according to claim 8, wherein the creating step further comprises, forming an ROI picture data elements of the ROI picture data matrix B2 from the combination of 10×10 to 30×30 adjacent pixels of the input picture data matrix B1.

10. The image processing method according to claim 1, wherein the frequency spectrum analysis comprises analyzing the frequency spectrum of the individual ROI picture data elements of the ROI picture data matrix B2 for finding undershooting or exceeding of values of the frequency spectrum of the individual ROI picture data elements relative to pre-defined threshold values.

11. The image processing method according to claim 10, wherein the redefined threshold values comprise organ-dependent threshold values.

12. The image processing method according to claim 1, wherein the histogram distribution analysis further comprises assigning to said at least object area a signal level of the ROI picture data elements which lies in a range of values from 10 to 70% of the histogram distribution.

13. The image processing method according to claim 12, wherein individual ROI picture data elements of the ROI picture data matrix B2 are analyzed by evaluation of their frequency spectrum as signal width analysis.

14. The image processing method according to claim 12, wherein evaluating the signal width function comprises, for each ROI picture data element forming the product of the digital units (du) of signal level and signal width and assigning each case of 300 to 5000 $du^2$ to the object area.

15. The image processing method as claimed in claim 1, further comprising, feeding the number of input units of a neuronal network from the analysis result of the individual ROI picture data elements and providing information from an output unit of the neuronal network as to which ROI picture data element is able to be assigned to the object area.

16. The image processing method in accordance with claim 1, wherein the signal evaluation of the ROI picture data elements of the object area for determination and setting of an optimized dosing power of the x-ray radiation is under-taken using the following steps:
   (a) forming the arithmetic mean of the signal levels of all ROI picture data elements of the object area;
   (b) forming a q-quantile from the mean values determined in step (a);
   (c) reconciling the value determined in step b) with the sensitivity of the x-ray detector for determining the system dose arriving at the x-ray detector; and
   setting the system dose.

17. The image processing method as claimed in claim 1, wherein the signal evaluation of the ROI picture data elements of the object area for determination and setting an optimized windowing comprises:
   Forming the arithmetic mean of the signal levels of all ROI picture data elements of the object area;
   Defining the lower window value by forming a q-quartile of the ROI picture data elements of the object area; and
   Defining the upper window value by forming a q-quartile of the ROI picture data elements of the object area.

18. An image processing method for determination and setting of dose control of images of a medical diagnostic device based on x-ray radiation, wherein a digitized image comprises a number of picture elements of a picture data matrix B originally created by an x-ray detector, the method comprising:
   composing the picture data matrix B to include at least an object area, at least a diaphragm area, and at least a direct irradiation area, wherein each of said respective areas has a different response to x-ray radiation passing through the respective areas, wherein respective picture data elements corresponding to said at least object area, said at least diaphragm area, and said at least direct irradiation area generate respective signals having different characteristics based on the different responses of the respective areas to the passing x-ray radiation, wherein the picture data matrix B is processed to identify among the respective areas said at least object area using the following steps:
   forming an input picture data matrix B1 starting from the original picture data matrix B;
   combining a number of pixels of the input picture data matrix B1 into Regions Of Interest (ROI);
   creating an ROI picture data matrix B2 comprising this ROI picture data elements, wherein each pixel of the input picture data matrix B1 is only involved once in the formation of an ROI picture data element;
   analyzing the individual ROI picture data elements of the ROI picture data matrix B2 to assign ROI picture data elements likely to correspond to one of said at least object area, said at least diaphragm area, and said at least direct irradiation area, wherein the analyzing of the individual ROI picture data elements of the ROI picture data matrix B2 comprises evaluating respective signals generated by the ROI picture data elements of the ROI picture data matrix B2, the evaluating based on the different responses of the respective areas to the passing x-ray radiation; and
   based on results from the evaluating of the respective signals generated by the ROI picture data elements of the ROI picture data matrix B2, selecting the ROI picture data elements of said at least object area, and discarding ROI picture data elements of said at least diaphragm area and said at least direct irradiation area
   wherein analyzing the individual ROI picture data elements further comprises:
      a frequency spectrum analysis that compares the frequency components of said individual ROI picture data elements to predefined threshold values;
      a histogram distribution analysis that determines a histogram range for each of said respective areas; and
      a signal width analysis that analyzes the signal widths of said individual ROI picture data elements.

* * * * *